US009962537B2

(12) United States Patent
Pravong et al.

(10) Patent No.: US 9,962,537 B2
(45) Date of Patent: May 8, 2018

(54) GAS INSUFFLATION AND SUCTION/IRRIGATION TUBING

(71) Applicant: Applied Medical Resources Corporation, Rancho Santa Margarita, CA (US)

(72) Inventors: Boun Pravong, Rancho Santa Margarita, CA (US); Kennii Pravongviengkham, Rancho Santa Margarita, CA (US); Nabil Hilal, Rancho Santa Margarita, CA (US); John R. Brustad, Rancho Santa Margarita, CA (US); Zoran Falkenstein, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 388 days.

(21) Appl. No.: 14/699,954

(22) Filed: Apr. 29, 2015

(65) Prior Publication Data

US 2015/0258323 A1 Sep. 17, 2015

Related U.S. Application Data

(63) Continuation of application No. 11/680,835, filed on Mar. 1, 2007, now abandoned.

(60) Provisional application No. 60/777,959, filed on Mar. 1, 2006.

(51) Int. Cl.
| | | |
|---|---|---|
| *A61M 39/08* | (2006.01) | |
| *A61M 1/00* | (2006.01) | |
| *A61M 13/00* | (2006.01) | |
| *F16L 11/115* | (2006.01) | |
| *F16L 11/15* | (2006.01) | |
| *F16L 27/12* | (2006.01) | |

(52) U.S. Cl.
CPC ............ *A61M 39/08* (2013.01); *A61M 1/008* (2013.01); *A61M 13/003* (2013.01); *F16L 11/115* (2013.01); *F16L 11/15* (2013.01); *F16L 27/12* (2013.01)

(58) Field of Classification Search
CPC ........ A61M 39/08; A61M 1/008; F16L 27/12; F16L 11/115; F16L 11/15
See application file for complete search history.

(56) References Cited

U.S. PATENT DOCUMENTS

| | | |
|---|---|---|
| 1,596,754 A | 8/1926 | Moschelle |
| 2,458,305 A | 1/1949 | Sanders |
| 2,836,181 A | 5/1958 | Tapp |
| 2,963,749 A | 12/1960 | Pavlic |
| 3,122,171 A | 2/1964 | Britton et al. |
| 3,388,705 A | 6/1968 | Grosshandler |
| 3,416,531 A | 12/1968 | Edwards |
| 3,585,707 A | 6/1971 | Stevens |
| 3,598,126 A | 8/1971 | Hoeltzenblem |
| 3,692,889 A | 9/1972 | Hetrich |

(Continued)

*Primary Examiner* — Bradley Osinski
(74) *Attorney, Agent, or Firm* — John F. Heal

(57) ABSTRACT

A medical tubing being flexible and kink-free as gas insufflation tubing and non-collapsible as suction/irrigation tubing is provided. The tubing is lightweight and thin-walled. The tubing has a generally rigid but thin walled with a structural shape or is generally soft and thin-walled tubing with a hard re-enforcement.

6 Claims, 8 Drawing Sheets

(56) References Cited

U.S. PATENT DOCUMENTS

| | | |
|---|---|---|
| 3,751,541 A | 8/1973 | Hegler |
| 3,794,080 A | 2/1974 | Huston et al. |
| 3,908,704 A | 9/1975 | Clement et al. |
| 3,913,622 A | 10/1975 | Holden |
| 3,919,367 A | 11/1975 | Maroschak |
| 4,000,341 A | 12/1976 | Matson |
| 4,017,244 A | 4/1977 | Vellani |
| 4,196,031 A | 4/1980 | Laikos et al. |
| 4,336,798 A | 6/1982 | Beran |
| 4,360,104 A | 11/1982 | Lang |
| 4,368,088 A | 1/1983 | Asakura et al. |
| 4,377,545 A | 3/1983 | Hornbeck |
| 4,593,690 A | 6/1986 | Sheridan et al. |
| 4,653,542 A | 3/1987 | Tascher |
| 4,737,153 A | 4/1988 | Shimamura et al. |
| 4,852,564 A | 8/1989 | Sheridan et al. |
| 4,873,048 A | 10/1989 | Jarvenkyla |
| 4,900,314 A | 2/1990 | Quackenbush |
| 4,966,202 A | 10/1990 | Bryan et al. |
| 4,990,143 A | 2/1991 | Sheridan |
| 4,998,527 A | 3/1991 | Meyer |
| 5,019,057 A | 5/1991 | Truckai |
| 5,139,730 A | 8/1992 | Holso et al. |
| 5,222,949 A | 6/1993 | Kaldany |
| 5,454,795 A | 10/1995 | Samson |
| 5,476,630 A | 12/1995 | Orsing |
| 5,538,513 A | 7/1996 | Okajima |
| 5,630,806 A | 5/1997 | Inagaki et al. |
| 5,695,483 A | 12/1997 | Samson |
| 5,702,373 A | 12/1997 | Samson |
| 5,720,504 A | 2/1998 | Stedman et al. |
| 5,755,704 A | 5/1998 | Lunn |
| 5,785,998 A | 7/1998 | Kolobow |
| 5,792,401 A | 8/1998 | Burnham |
| 5,795,341 A | 8/1998 | Samson |
| 5,827,242 A | 10/1998 | Follmer et al. |
| 5,947,940 A | 9/1999 | Beisel |
| 6,021,816 A | 2/2000 | Jeltsch et al. |
| 6,102,078 A | 8/2000 | Kramer, Jr. |
| 6,258,080 B1 | 7/2001 | Samson |
| 6,394,145 B1 | 5/2002 | Baily |
| 6,398,266 B1 | 6/2002 | Crump |
| 6,554,820 B1 | 4/2003 | Wendlandt et al. |
| 6,569,148 B2 | 5/2003 | Bagaoisan et al. |
| 6,616,651 B1 | 9/2003 | Stevens |
| 6,626,889 B1 | 9/2003 | Simpson et al. |
| 6,764,627 B2 | 7/2004 | D'Angelo |
| 6,793,621 B2 * | 9/2004 | Butler ............... A61B 1/00154 600/114 |
| 7,811,253 B2 | 10/2010 | Hart et al. |
| 7,942,862 B2 | 5/2011 | Hart et al. |
| 8,028,395 B2 | 10/2011 | Taylor et al. |
| 8,105,285 B2 | 1/2012 | Hart et al. |
| 2003/0009151 A1 | 1/2003 | Wang |
| 2004/0102804 A1 | 5/2004 | Chin |
| 2004/0153049 A1 | 8/2004 | Hewitt et al. |
| 2004/0210281 A1 | 10/2004 | Dzeng et al. |
| 2005/0010194 A1 | 1/2005 | Zhou |
| 2005/0043713 A1 | 2/2005 | Zhou |
| 2005/0119686 A1 | 6/2005 | Clubb |
| 2005/0161101 A1 | 7/2005 | Wisdom et al. |
| 2005/0165366 A1 | 7/2005 | Brustad et al. |
| 2005/0177168 A1 | 8/2005 | Brunnett et al. |
| 2006/0001263 A1 | 1/2006 | Hegler |

* cited by examiner

GAS INSUFFLATION AND SUCTION/IRRIGATION TUBING

CROSS-REFERENCE TO RELATED APPLICATIONS

This application is a continuation of U.S. patent application Ser. No. 11/680,835, entitled "GAS INSUFFLATION AND SUCTION/IRRIGATION TUBING," filed Mar. 1, 2007, which claims the benefit of U.S. Provisional Application No. 60/777,959 filed Mar. 1, 2006, the disclosures of which are each hereby incorporated by reference as if set forth in full herein.

BACKGROUND

The present invention generally relates to tubing used in surgical procedures and, in particular, gas insufflation and suction/irrigation tubing.

In surgical procedures employing tubing, it is desirable to utilize tubing that is quite flexible and light weight. This is desired as the tubing typically connects from an apparatus outside the sterile field to a connection point at the patient site where it will be within the working field of the surgical staff. Rigid, stiff and non-flexible tubing is often less desirable being inconvenient or cumbersome to work with.

Medical tubing is largely tubing, where tradeoffs of features, such as flexibility, lightweight, kink-free, and non-collapsible are common.

SUMMARY

In general, high mechanical flexibility and being kink-free are especially of interest for gas insufflation tubing while being non-collapsible is especially of interest for suction/irrigation tubing. Being lightweight and thin-walled are desirable for both applications. Various aspects of various medical tubing being convenient, such as being flexible and lightweight, and functional, such as being kink-free and non-collapsible are provided. Such a combination can be met by providing generally rigid but thin-wall tubing with a structural shape or by providing generally soft and thin-walled tubing with a generally hard re-enforcement.

A flexible, kink-free, non-collapsing and lightweight medical tubing to communicate either a vacuum and/or a stream of gas or fluid from/to the surgical site, introducing carbon dioxide in gas insufflation systems for laparoscopic procedures, the respective utilization of a vacuum or a saline solution for suction/irrigation systems in laparoscopy or general surgery, is provided. At the same time and sometimes depending on the application, tubing having a kink-free, non-collapsing or pressure-resistant arrangement can seem to contradict flexibility. For example, for the tubing in suction/irrigation systems where the tubing can sustain working pressures of about 16 psi, or a vacuum of about 1 Torr, respectively.

In one aspect, a gas insufflation, suction and irrigation medical tubing is provided. The tubing comprises a tubular body having a proximal end, a distal end and a lumen. The lumen extends from the proximal end to the distal end of the tubular body and a support is coupled to the tubular body. The support is less compliant than the tubular body.

In one aspect, a gas insufflation, suction and irrigation medical tubing is provided. The tubing comprises a tubular body having a proximal end, a distal end and a lumen. The lumen extends from the proximal end to the distal end of the tubular body and a support is coupled to the tubular body. The support is less compliant than the tubular body. The tubular body is housed in housing of a container in which the housing has a shaft enclosed in and connected to the housing.

In one aspect, a gas insufflation, suction and irrigation medical tubing comprises a lightweight tubular body having a proximal end, a distal end and a lumen. The lumen extends from the proximal end to the distal end of the tubular body. A support is coupled to the tubular body and has means for increasing flexibility, resisting kinks and withstanding vacuum and irrigation pressures.

Many of the attendant features of the present invention will be more readily appreciated as the same becomes better understood by reference to the foregoing and following description and considered in connection with the accompanying drawings in which like reference symbols designate like parts throughout.

DETAILED DESCRIPTION

Figure 1A:
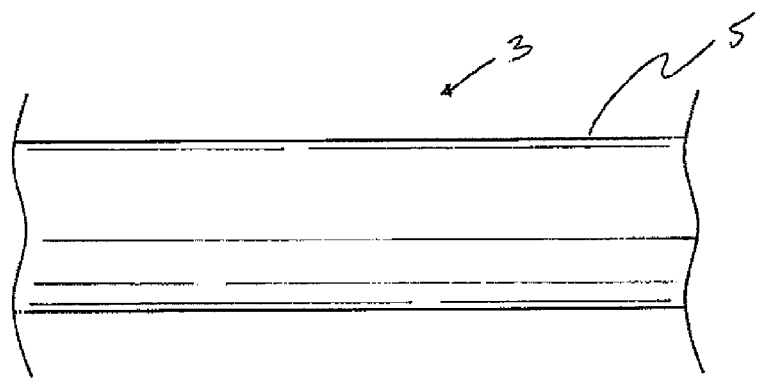
FIG. 1A is a side view of medical tubing with a single lumen.
Figure 1B:
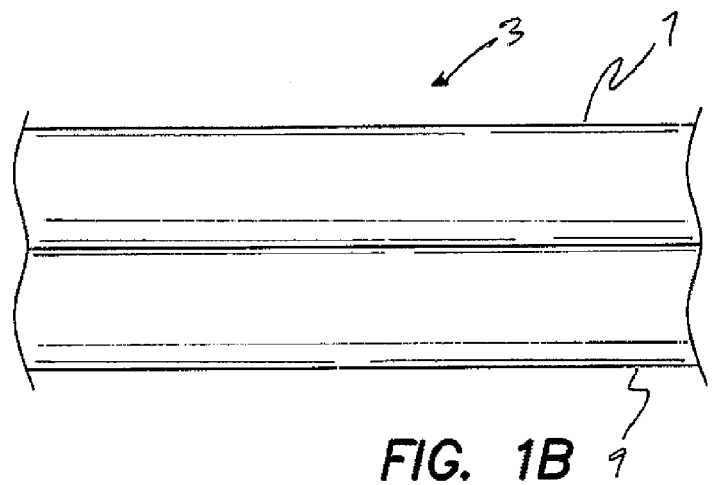
FIG. 1B is a side view of medical tubing with multiple lumens.

Referring now to FIGS. 1A and 1B, medical tubing 3 comprises of straight-walled plastic tubing. The tubing 3 can carry either single or multi-lumen conduits, and can comprise of single tube 5 or multiple tubes 7,9. In one aspect, the multiple tubes 7,9 are permanently attached to each other. The manufacturing process utilized is an extrusion process.

The optimization of both material hardness and wall thickness calls for generally soft plastic material with moderate wall thickness (1-2 mm). The optimization reflects a compromise between being kink-free, flexibility and vacuum compatible (i.e., preventing the tubing to collapse radially under vacuum).

Figure 2:
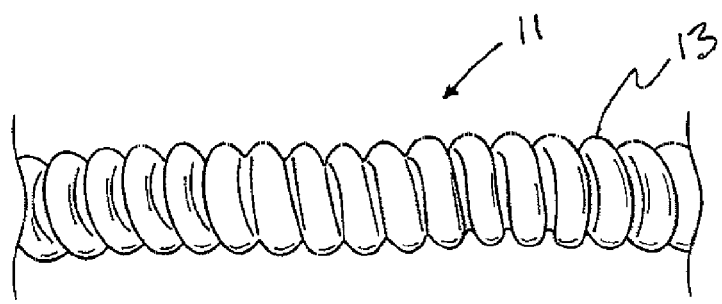
FIG. 2 is a side view of convoluted medical tubing in accordance with various aspects of the present invention.

FIG. 2 illustrates a structural re-enforcement of a thin-walled (sub-mm), but generally stiff tubing 11. As such, medical tubing 11 having a generally rigid wall that utilizes a convoluted tube shape 13 as structural enforcement of the tubing is provided. In comparison to unshaped (straight) tubing, the convoluted shape enables the tubing to be both flexible and kink-free. In difference to conventional "straight" tubing, the tubing shows a spiral-like enlargement 13 of the tube diameter. The wall thickness at the convolutions 13 remains the same as the remaining tubing. The convolutions allow the tubing to be flexible, while the generally stiff wall material enables the tubing to be vacuum-compatible (i.e., to resist radial compression). At the same time, the increased overall tube diameter at the convolution sites enables the tube to be kink-free when being bent or coiled. Because of the structural enforcement, the thin walled tubing can be applied for both pressure and vacuum cases.

The convolution 13 of the tubing 11 also re-enforces the tube regarding radial and axial compression, which makes the tubing vacuum compatible. Manufacturing processes for this kind of tubing in one aspect comprises of blow-molding, where a (straight) tubing would be placed in the center of a mold, and applied with some positive (air) pressure while being heated. As a result, the (straight) tubing expands to take the shape of the mold. While the process of blow molding can be restricted to production of defined lengths of tubing, a blow extrusion process enables the continuous production of this type of tubing. Here, a (straight) tube is being extruded and fed into two moving "mold-like" blocks. Similarly to blow molding, application of positive pressure into the tube (while being extruded) allows the tube to take the convoluted shape. Continuous movement of the "mold-like" blocks on a rotating conveyor assembly enables production of continuous lengths of the tubing.

Figure 3:
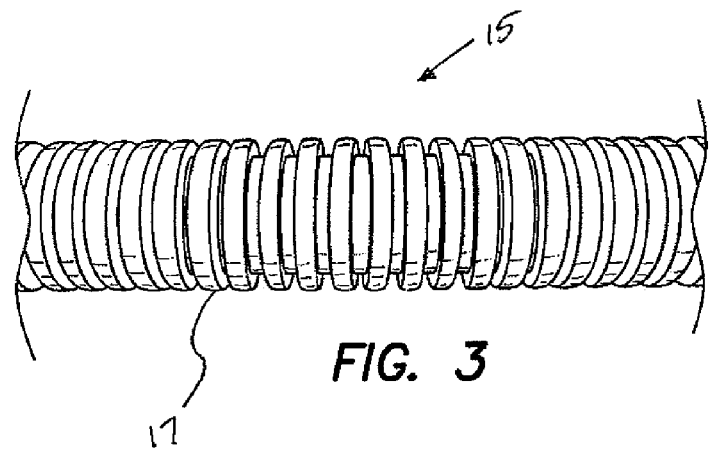
FIG. 3 is a side view of corrugated medical tubing in accordance with various aspects of the present invention.

In FIG. 3, a structural re-enforcement thin-walled (sub-mm) stiff tubing 15 is shown. As such, a medical tubing 15 that utilizes a corrugated shape 17 as structural enforcement of the tubing is provided. The tubing provides ring-like enlargements 17 of the tube diameter where the wall thickness at the corrugated remains the same as the remaining tubing. The periodic corrugations 17 allow the tubing to be flexible, while the generally stiff wall material enables the tubing to be vacuum-compatible (i.e. to resist radial compression). At the same time, the increased overall tube diameter at the corrugation sites enables the tube to be kink-free when being bent or coiled.

In comparison to unshaped (straight) tubing, the corrugated shape also enables the tubing to be both flexible and kink-free. Similar to the convoluted re-enforcement, the corrugation of the tubing also re-enforces the tube regarding radial and axial compression, which makes the tubing vacuum compatible. Manufacturing processes for corrugated tubing comprises of blow-molding and blow extrusion. In difference to convoluted tubing, corrugated tubing can be compressed axially. Depending on the shape of the corrugation, the corrugations can (permanently) "collapse" on themselves, which permanently reduces the size of the tubing. The tubing can again be expanded to its original length by pulling axially on the tubing.

Figure 4A:
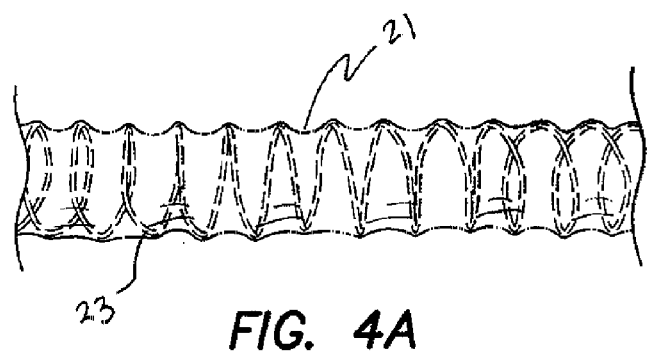
FIG. 4A is a side view of a reinforced convoluted medical tubing in an expanded or resting state in accordance with various aspects of the present invention.
Figure 4B:
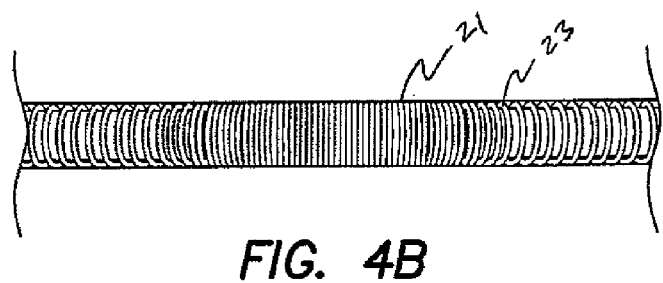
FIG. 4B is a side view of a reinforced convoluted medical tubing in a compressed state in accordance with various aspects of the present invention.

FIGS. 4a and 4b illustrate a generally thin and soft tube 21 with a generally hard structural re-enforcement 23. As such, in one aspect, medical tubing 21 that utilizes a mechanical re-enforcement 23 within soft and/or straight-walled tubing is provided. An example of such a re-enforcement is shown as a metallic and/or plastic coiled wire. The coiled wire 23 is connected to the thin and soft outer tube wall. The generally thin wall of the tube 21 allows axial compression (and size reduction) of the tube 21, while the generally hard coiled wire 23 prevents radial compression. If the spiral coil is also stiff enough in axial direction, this tubing can also be used for vacuum applications and can be very kink-resistant. To reduce the overall length of the tubing during storing, the tube can be mechanically compressed axially, as shown in FIG. 4b.

In comparison to unshaped (straight) tubing, the re-enforcement 23 allows the use of a thinner tube wall of tube 21 to be both flexible and kink-free. Depending on the material and material thickness of both the tube wall and the re-enforcement, the arrangement can also sustain radial and axial compression, which makes the tubing vacuum compatible. Examples of such tubing in one aspect would be a (steel) braided mesh, which is encapsulated within (thin-walled) straight tubing. An extrusion, molding, other types of processes, such as one described in U.S. patent application Ser. No. 10/766,138, filed Jan. 28, 2004, the disclosure of which is hereby incorporated by reference as if set forth in full herein, or a combination of processes, can accomplish the coating process of, for example, coating a braided mesh within thin-walled tubing. Another example for this type of tubing is the encapsulation of a (stiff) spiral coil within (soft) straight tubing. Potential manufacturing processes include co-extrusion, extrusion of a straight tube over the coil, or other similar processes referenced above of two similar materials. Depending on the shape, material and material thickness used, the corrugations can also enforce the tubing axially, which allows the use of this type of tubing for vacuum applications.

Figure 5:
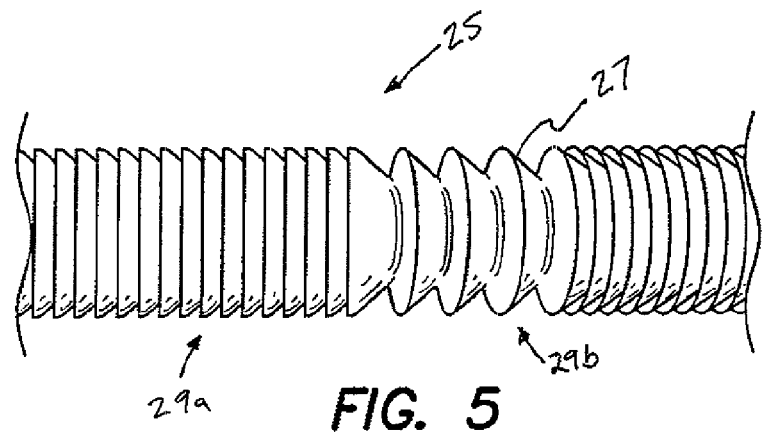
FIG. 5 is a side view of corrugated tubing having asymmetric corrugations in accordance with various aspects of the present invention.

In FIG. 5, corrugated tubing 25 with periodic tube enlargements 27 are asymmetric in shape. The shaping of the corrugations 27 allow the corrugations to "collapse" on themselves during axial compression, which depending on the overall tube diameter can reduce the effective length of the tubing 27. For example, ratios for expanded to collapsed tube lengths can range from 1.5 to 4 for tube diameters ranging from ¼" to about 1". When releasing the radial compression, the tubing 27 remains "compressed" as the corrugations "snap" into the collapsed state. In FIG. 5, tube sections are shown in both a compressed 29a and an extended state 29b. At the same time, the collapsible tubing remains flexible in both an extended and a collapsible state. However, the high flexibility in the axial direction can cause the collapsed (extended) tubing applied with pressure (vacuum) to be forced into its extended (collapsed) state.

Figure 6A:
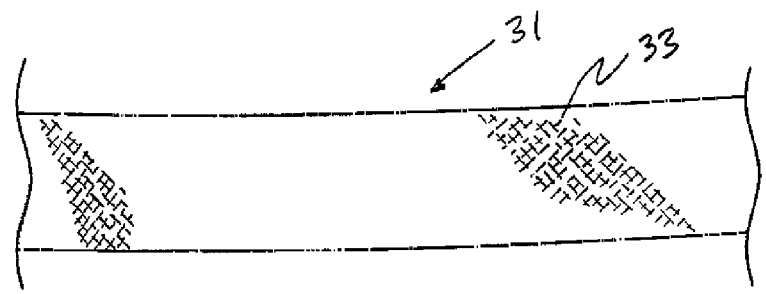
FIGS. 6A-6B are side views of reinforced medical tubing in accordance with various aspects of the present invention.
Figure 6B:
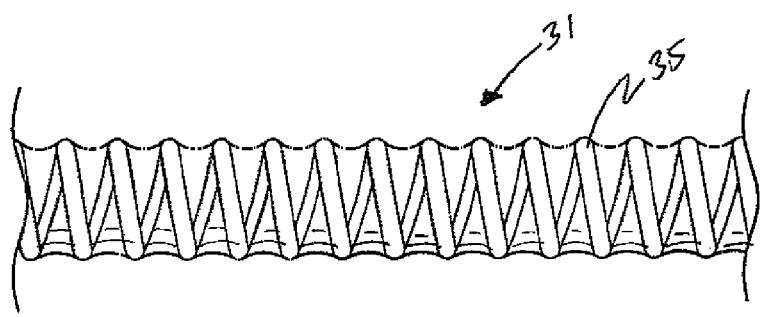

In one aspect, as shown in FIGS. 6A,B, medical tubing 31 with structural re-enforcements 33, 35 are provided. The soft tubing 31 is re-enforced by an encapsulated, generally stiff mesh 33. While the soft tube material allows the tubing 31 to be flexible, the generally hard plastic or metallic mesh 33 provides mechanical support for the tubing to be kink-free and vacuum resistant. In FIG. 6B, an encapsulated coil 35 gives the structural re-enforcement of thin-walled, generally soft tubing 31. The generally soft and thin tube material allows the tube 31 to be flexible and the encapsulated generally hard coil 35 prevents the tube from kinking on itself. When the spiral coil is sufficiently stiff in axial direction, this tubing can also be vacuum resistant.

In one aspect, a combination of several types of tubing is provided that allows a combination of applications. An example that illustrates such a combination would be placing straight tubing into corrugated or convoluted (i.e., a very flexible and kink-free) tubing. While the inner tubing can be applied with vacuum (while not collapsing axially or radially), the lumen between the inner and outer tube can be applied with pressure (such as from an irrigation fluid). This arrangement is of particular interest for a suction/irrigation system that allows high flexibility being lightweight, while not collapsing and/or extracting under vacuum pressure.

Figure 7:
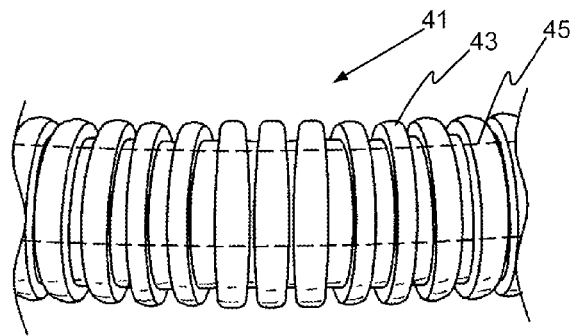
FIG. 7 illustrates a side view of dual concentric medical tubing in accordance with various aspects of the present invention.

Referring to FIG. 7, in one aspect, a medical tubing 41 with one tube 43 positioned inside another tube 45 to combine two different types of tubing is provided. This configuration can provide the simultaneous application of vacuum to the inner tube, and pressurized fluid to the outer tube or vice versa, e.g., for use in suction/irrigation systems. While the (vacuum-compatible) inner tubing prevents both tubes from collapsing axially under vacuum, the thin-walled outer tubing will allow for kink-free flexibility of both tubes.

Figure 8:
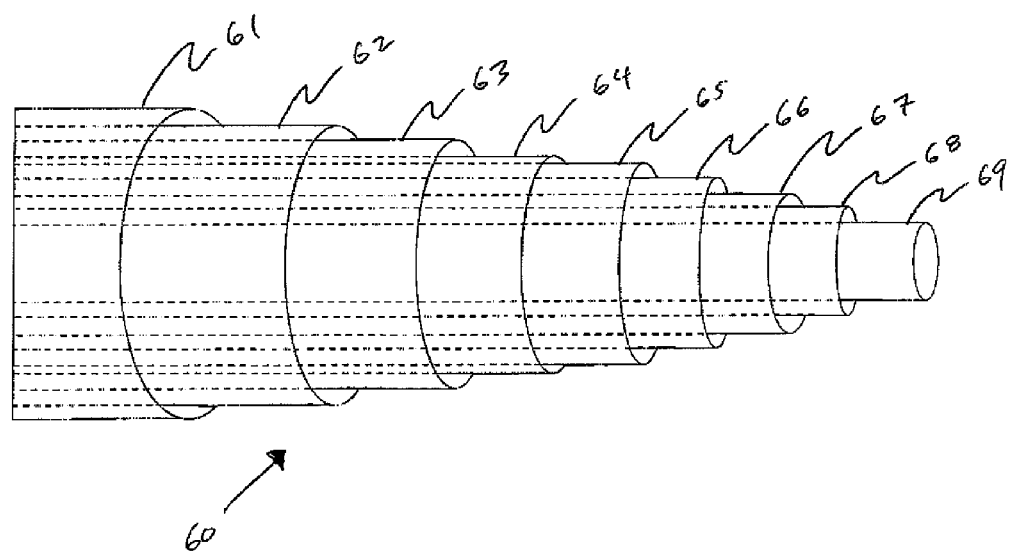
FIG. 8 is a perspective view of telescopic medical tubing in accordance with various aspects of the present invention.

Referring to FIG. 8, a size (axial) reduction of a straight-walled tubing 60 is shown. Tube sections 61-69 of various diameters and/or of various lengths are nested into each other. The inner and outer wall diameters of adjacent tube sections in one aspect are configured to deliver a snug fit, allowing sealing of the tubing. The tubing can be extended into a telescope-like manner by axially moving or pulling on the tubing.

Figure 9A:
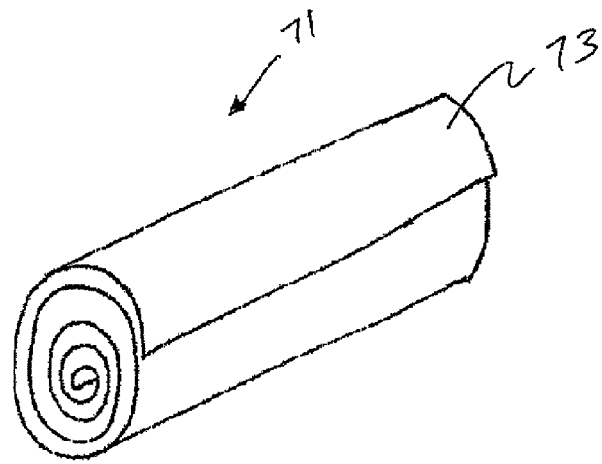
FIGS. 9A, B are perspective views of spiraled medical tubing in accordance with various aspects of the present invention.
Figure 9B:
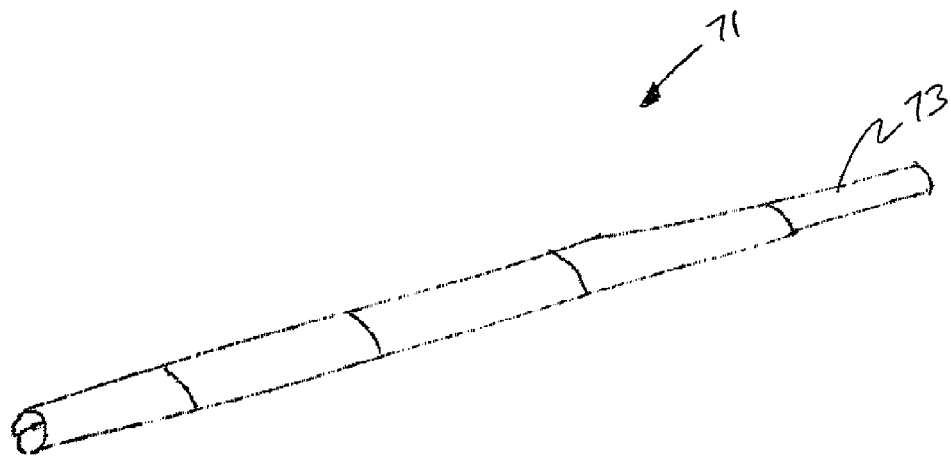

Referring to FIGS. 9A-B, in one aspect, the spiraled medical tubing 71 is generated by wrapping a tube wall 73 multiple times over itself. In one aspect, by pulling one of the outer most ends away from the opposing innermost end of the overlaying tube wrapping can vary the length of the tube.

Figure 10A:
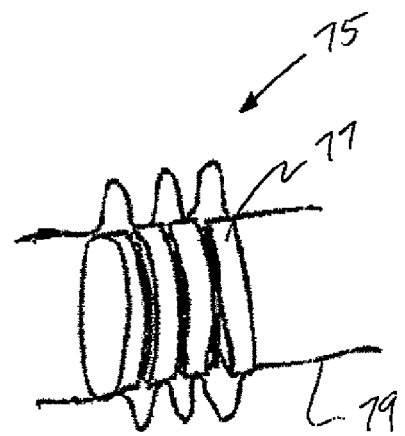
FIGS. 10A, B are perspective views of collapsible medical tubing in accordance with various aspects of the present invention.
Figure 10B:
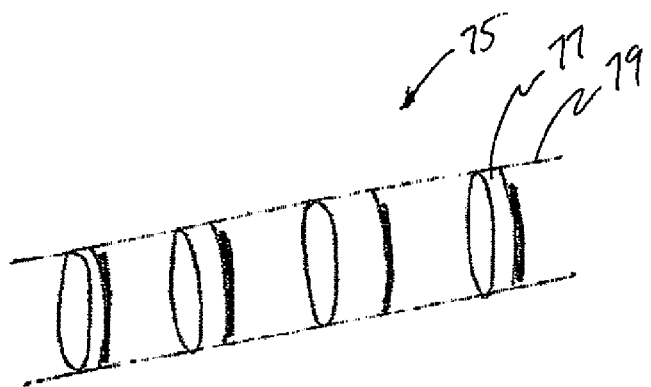

FIGS. 10a and 10b depict in one aspect a collapsible tubing 75 comprising inner rings 77 of a hard durometer that are connected to soft and thin-walled outer tubing 79. The inner rings are provided with a functional profile or configuration in that consecutive rings snap-fit to each other, thereby allowing reduction of the overall tube length and in various aspects a permanent reduction. When pulling axially on the tubing, the snap-fitted rings can be disengaged, thereby increasing the overall length of the tubing. While this tubing is well suited for conducting pressurized gas or fluids, the tubing may be less suited for vacuum applications, as the thin-walled tube can axially collapse under vacuum.

Figure 11A:
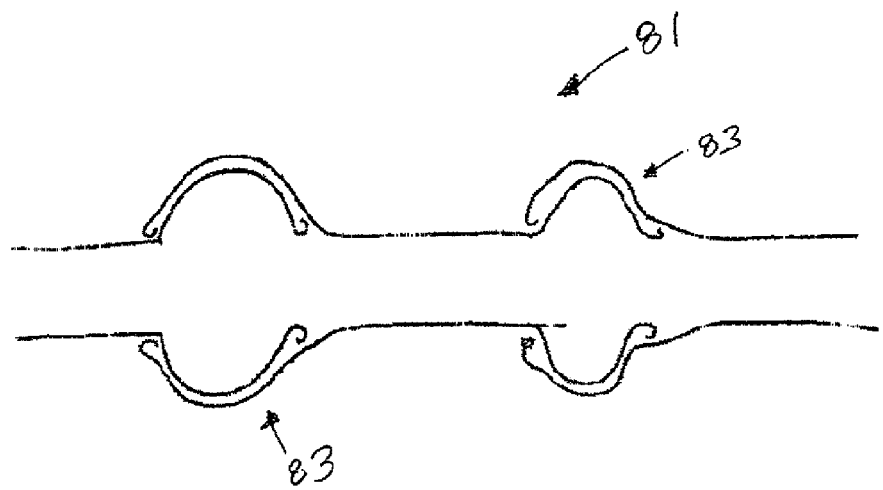
FIGS. 11A, B are cross-sectional side views of "ball-and-socket" medical tubing in accordance with various aspects of the present invention.
Figure 11B:
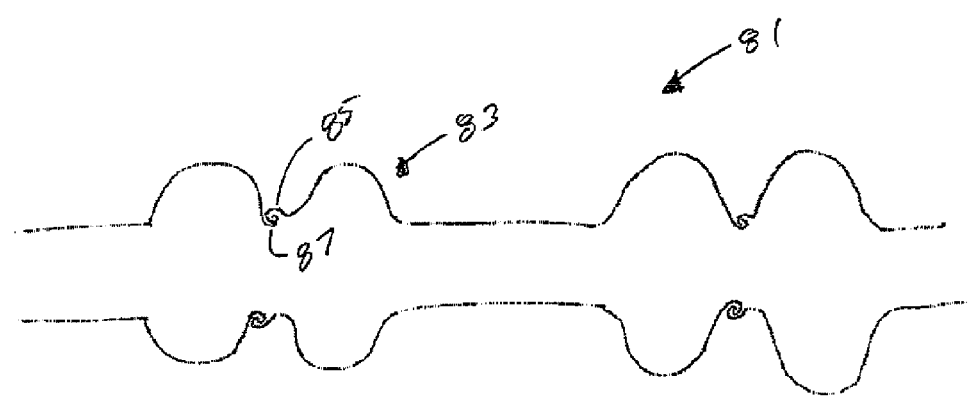

FIGS. 11a and 11b show another aspect of corrugated or convoluted tubing 81 where periodic tube portions or section 83 comprises of "ball-and-socket" arrangements. The tubing becomes collapsible by having neighboring elements "ball" 85 and "socket" 87 and vice versa nesting into each other, respectively. The shaping of the corrugations or convolutions allow the tubing to "collapse" during axial compression, or to "extend" during axial pull, which depending on the overall tube diameter can change the effective length of the tubing.

Figure 12:
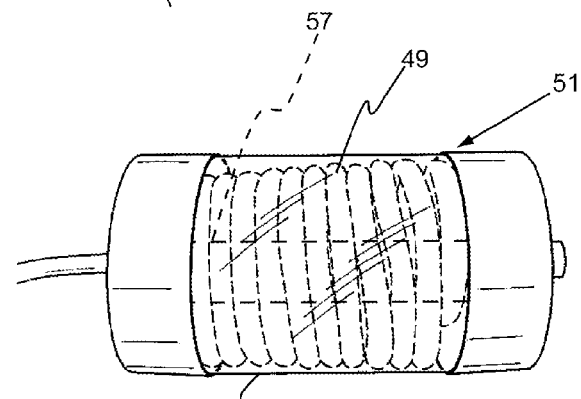
FIGS. 12-13 are side views of a storage or container for holding medical tubing such as those provided in reference to FIGS. 1 through 10 or described throughout this specification in accordance with various aspects of the present invention.
Figure 13:
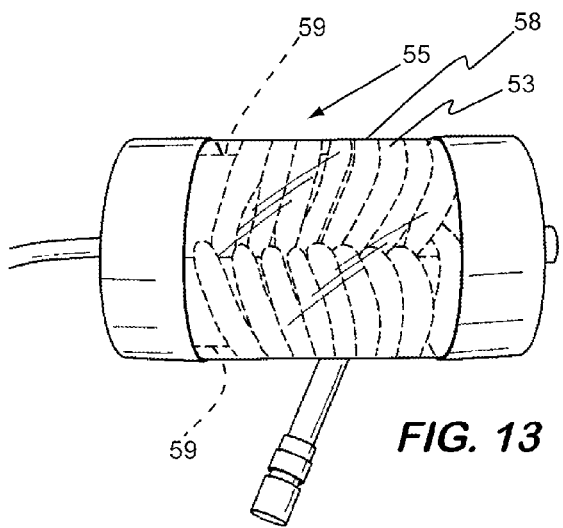

Referring now to FIG. 12, packaging or storage arrangement is shown. The tubing 49 is stored in a coiled fashion inside a storage container 51 that has a housing 56 and a shaft 57 enclosed in, and connected to, the housing. In one aspect, the tubing 49 is wrapped around the shaft 57. By pulling the tubing out of the container, any needed length of tubing can be dispensed. In FIG. 13, the tubing 53 is stored in a double-coiled fashion inside a storage container 55 that has a housing 58 and two parallel shafts 59 enclosed in, and connected to, the housing. The double coiling of the tubing 53 in one aspect is generated by wrapping the collapsed or compressed tubing around the two shafts 59, either encircling the shafts or in a "figure eight" pattern, which prevents twisting of tubing when dispensing the tubing from the container 55. For example, when pulling the tubing out of the container to dispense any needed length of tubing, twisting (which can lead to kinking) of the tubing is prevented. In one aspect, the shafts 57, 59 in FIGS. 12 and 13 are rotatable.

Various aspects of kink-resistant and flexible plastic tubing are provided for utilization with surgical instrumentation, such as in gas insufflation systems and/or suction/irrigation system in laparoscopic or general surgery. Generally, in various aspects, the tubing is mechanically flexible and kink-resistant due to the structural enforcement of a thin wall, which makes the tubing also lightweight. Examples are of various aspects are provided for corrugated, convoluted and also collapsible tubing, as well as tube structures that utilize coiled or braided wall-enforcements. Combination of various tubes provides a mechanical enforcement that can allow simultaneous application of vacuum/pressure, such as for suction/irrigation systems. Continuous plastic extrusion, co-extrusion, blow-mold, or over-mold processes can produce the various aspects of various tubing provided. Various aspects of various packaging and/or storing of various tubes are also provided that can, for example, provide small-sized tube dispensers.

Accordingly, the present invention provides gas insufflation, suction and irrigation medical tubing. Although this invention has been described in certain specific embodiments, many additional modifications and variations would be apparent to those skilled in the art. It is therefore to be understood that this invention may be practiced otherwise than specifically described, including various changes in the size, shape and materials, without departing from the scope and spirit of the present invention. Thus, embodiments of the present invention should be considered in all respects as illustrative and not restrictive, the scope of the present invention to be determined by the appended claims and their equivalents rather than the foregoing description.

The invention claimed is:

1. A gas insufflation, suction and irrigation tubing system comprising:
   a first tube section comprising thin-walled tubular body, the tubular body having a proximal end, a distal end and a lumen, the lumen extending from the proximal end to the distal end of the tubular body;
   the tubular body comprising a wall having a structural enforcement configuration defined by periodic enlargements of an outer diameter of the tubular body, the periodic enlargements having a radial enforcement component being arranged to resist radial compression and an axial enforcement component being arranged to resist axial compression; and
   a second tube section having an outer diameter configured to engage with a snug fit to one of the proximal end and the distal end of the first tube section such that the first tube section and the second tube section can be sealingly combined to have an extended axial length and separated to have a reduced axial length;
   wherein the second tube section can be nested into the first tube section with the reduced axial length; and
   wherein the second tube section is telescopically extendable between the reduced axial length and the extended axial length.

2. The tubing system of claim 1, wherein the tubing is configured to sustain working pressures of 16 psi.

3. The tubing system of claim 1, wherein with the first tube section and the second tube section combined in the reduced axial length, the first and second tube sections are nested in a ball and socket arrangement.

4. The tubing system of claim 1, wherein the tubular body has a wall thickness of less than 1 mm.

5. The tubing system of claim 1, wherein the periodic enlargements are formed by a blow molding process.

6. The tubing system of claim 1, wherein the periodic enlargements are formed by a blow extrusion process.

* * * * *